(12) United States Patent
Hallberg et al.

(10) Patent No.: US 7,381,550 B2
(45) Date of Patent: Jun. 3, 2008

(54) INTEGRATED PROCESS FOR PRODUCING "CLEAN BEEF" (OR MILK), ETHANOL, CATTLE FEED AND BIO-GAS/BIO-FERTILIZER

(75) Inventors: David E. Hallberg, Omaha, NE (US); Victor W. Schlesinger, Omaha, NE (US)

(73) Assignee: Prime Bioshield, LLC., Omaha, NE (US)

( * ) Notice: Subject to any disclaimer, the term of this patent is extended or adjusted under 35 U.S.C. 154(b) by 478 days.

(21) Appl. No.: 10/752,531

(22) Filed: Jan. 8, 2004

(65) Prior Publication Data

US 2005/0153410 A1 Jul. 14, 2005

(51) Int. Cl.
C12P 7/06 (2006.01)
A23K 1/00 (2006.01)

(52) U.S. Cl. ..................... 435/161; 426/635

(58) Field of Classification Search ........... 435/161; 426/635
See application file for complete search history.

(56) References Cited

U.S. PATENT DOCUMENTS

| | | | | |
|---|---|---|---|---|
| 72,827 | A | 12/1867 | Embree | 426/624 |
| 87,397 | A | 3/1869 | Christie et al. | 426/624 |
| 2,158,043 | A | 5/1939 | Grelck | 426/624 |
| 4,018,188 | A | 4/1977 | Burdette | 119/28 |
| 4,356,269 | A | 10/1982 | Thomsen et al. | 435/316 |
| 4,400,195 | A | 8/1983 | Rijkens | 71/10 |
| 4,503,154 | A | 3/1985 | Paton | 435/167 |
| 5,047,332 | A | 9/1991 | Chahal | 435/32 |
| 6,355,456 | B1 * | 3/2002 | Hallberg et al. | 435/161 |
| 2004/0025715 | A1 * | 2/2004 | Bonde et al. | 99/485 |

OTHER PUBLICATIONS

"Gobar Gas" by Methane Experiments in India. 1971. Mother Earth News, Issue No. 12, November/December, pp. 1-6.*
Hallberg . 2003.Integrated Biorefinery Complexes: Energy and Food Security, & Rural Development. Presented to the Governor's Ethanol Coalition, Sioux Falls, SD.*
Evaluation of Corn and Sorghum Distillers Byproducts, Lodge et al, pp. 37-43, 1997.
1999 Nebraska Beef Report, p. 32, Fanning et al.
Proceedings of the American Society of Animal Science, 1999, Stock et al, 1-12.
Evaluation of Wet Distillers Composite for Finishing Ruminates, Lodge et al, pp. 44-50, 1997.
Feeding Value of Wet Distillers Byproducts for Finishing Ruminants, Larson et al, pp. 2228-2236, 1993.
Uses of Corn Coproducts in Beef and Dairy Rations, Klopfenstein et al, 2001.
Evaluation of Wet Distillers Grains in Finishing Diets for Yearling Steers, A.S. Leaflet R1450, 1997.
Substituting Wet Distillers Grains for Condensed Distillers Solubles for Corn Grain in Finishing Diets for Yearling Heifers, A.S. Leaflet R1451, 1997.
Evaluation of Wet and Dry Distillers Grains and Wet and Dry Corn Gluten Feeds for Ruminants, Firkins et al, Journal of Animal Science, vol. 60, No. 3, 1985.
Wet Corn Distillers Byproducts Compared with Dried Corn Distillers Grains with Solubles as a Source of Protein and Energy for Ruminants, Ham et al, pp. 3246-3257, 1994.
Evaluation of Wet Distillers Grains for Finishing Cattle, A.S. Leaflet 1342, 1997.

* cited by examiner

*Primary Examiner*—Jon Weber
*Assistant Examiner*—Kailash Srivastava
(74) *Attorney, Agent, or Firm*—Bacon & Thomas, PLLC

(57) ABSTRACT

An ethanol unit and anaerobic digestion/bio-fertilizer unit are integrated with a cattle feedlot (or dairy operation), wherein a continuous, balanced process yields a sanitary, low- to zero-pollution, and economically efficient production of "clean beef" (or milk), fuel ethanol, and bio-gas/bio-fertilizer. Fossil fuel consumption is substantially reduced, even eliminated, and 100% of the cattle waste is treated in digesters wherein it is converted into medium-BTU gas (bio-gas), organic fertilizer and bio-compost. The ethanol unit serves the purposes of ethanol production, grain pretreatment to produce feed for the cattle and production of a thin stillage which is fed to the digesters. The grain is first processed in the ethanol unit, where the starch portion is converted into ethanol and $CO_2$. The remaining portion is separated into the thin stillage and a wet cake which is fed directly to cattle as a superior ruminant animal ration which displaces certain traditional feed components, alters the standard starch to protein ratio, and significantly improves conversion efficiencies and meat/milk quality.

10 Claims, 4 Drawing Sheets

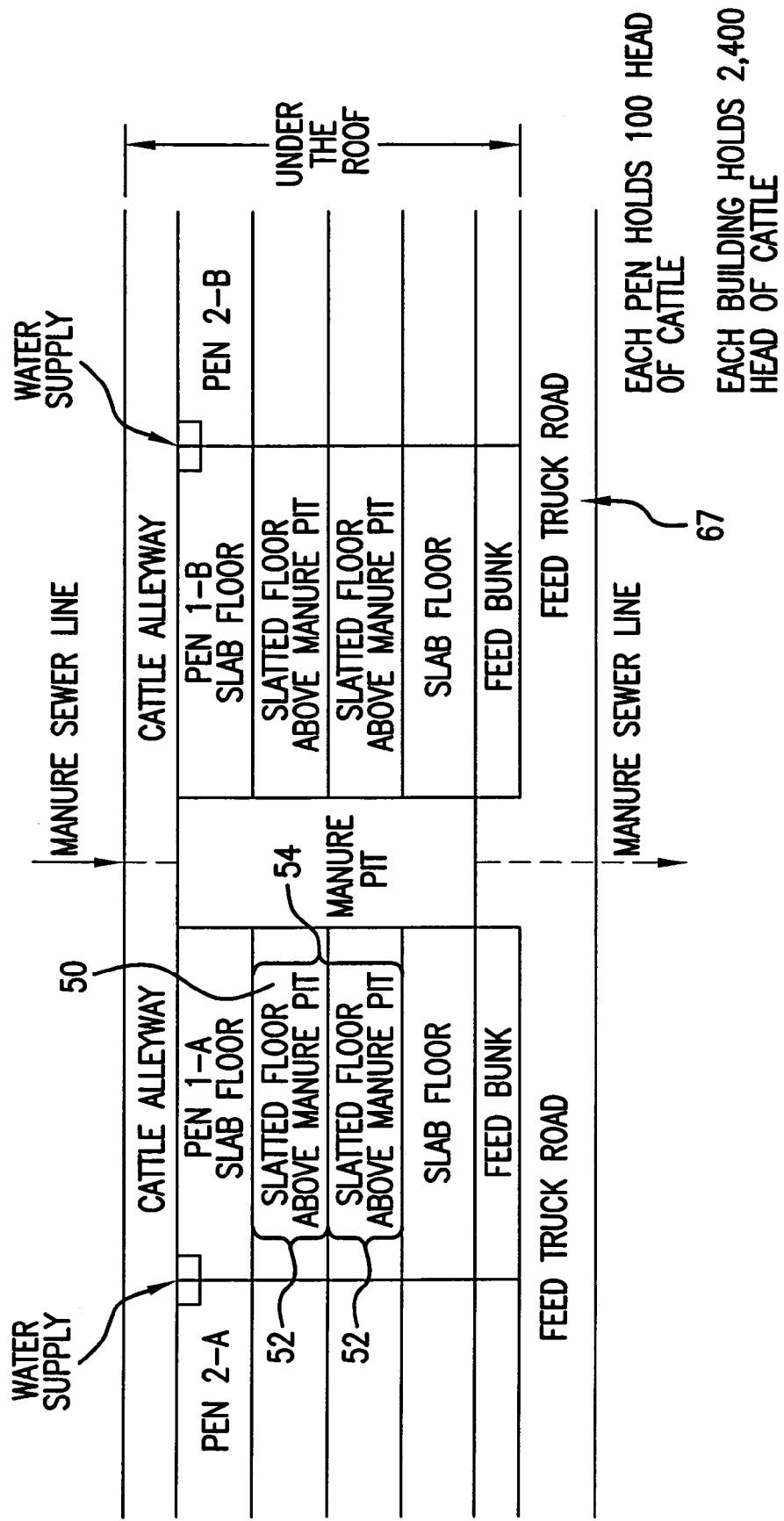

INTEGRATED PROCESS FOR PRODUCING "CLEAN BEEF" (OR MILK), ETHANOL, CATTLE FEED AND BIO-GAS/BIO-FERTILIZER

BACKGROUND OF THE INVENTION

1. Field of the Invention

The present invention relates to a novel integrated process for the environmentally benign use of grains and renewable materials to produce "clean beef" (or milk), fuel ethanol for motor fuel purposes, and bio-gas/bio-fertilizer from animal wastes and other residual streams.

2. Background of the Prior Art

Agriculture in general, and the livestock feeding industry in particular, face increasing pressures which pose challenges to traditional methods of doing business, and offer opportunities to those with improved methods. Trends in the marketplace have created a demand for beef and diary products that are high quality, and verifiably safe. Environmental authorities at both the national and local levels are imposing requirements on concentrated animal feeding operations (CAFOs) to ensure that odor and environmental contamination are substantially reduced from current levels. Cost effective methods of converting animal wastes into marketable fuels and products are needed. Public policy is encouraging substantial expansion in fuel ethanol production but conventional ethanol technology relies heavily on purchased natural gas to generate steam for operations, and high natural gas costs have stifled capital investment in new plants. To the greatest extent possible, all of these methods and products should be generally "sustainable" (e.g., renewable) and environmentally friendly.

In conventional practice, beef cattle are normally fed 22 pounds of dry matter equivalent per day with as much as a 50% moisture content for a total feed weight of approximately 44 pounds per day. The moisture content represents a portion of the animal's total daily water intake. Cattle on average convert 6.5 pounds of feed into one pound of body weight gain. If the animal gains 3.5 pounds of weight per day and requires 6.5 pounds of feed per pound of gain, it must consume 22.75 pounds of dry matter feed per day. This diet not only allows for weight gain but provides the energy to sustain the animal in good health. Dairy cows, which like beef cattle, are ruminant animals, require approximately 50 pounds of dry matter intake per day to support milk production. Approximately 70% of the animal's dry matter feed ration is digestible. The non-digestible and water portions are passed as manure and urine which in conventional practice are typically dumped onto the ground. The pens are then occasionally cleaned by scraping the manure and dirt mixture into wind row piles where it sun-dries. The mixture is eventually field applied, sold as fertilizer or disposed of in some fashion. Due to growing environmental concerns, however, manure management is rapidly becoming one of the most critical functions in CAFOs.

Modern feedyards are designed to catch the water runoff from cattle pens in special drain basins or pits which are often aerated to introduce more oxygen into them. The water will evaporate as new runoff continuously refills the pits. They are designed to normally handle up to a 25-year rain runoff. However, in just the last 25 years, there have been not only 25-year rains but a 50, 100 and even a 300-year rain in the Midwest. These heavy rains can, and do, overwhelm the feedyards' ability to manage the pen drainage systems.

Dairies, although historically smaller, encounter similar manure pollution challenges.

Since the early 1990's, many states and the federal government have begun to review the public policies regulating CAFOs. Many complaints have been received from environmentalists, naturalists, fishermen and neighbors regarding the untreated contamination resulting from the feedyards. The sheer volume of cattle waste (12 times that of one adult human per day) is cause for considerable concern. Whereas human waste is treated in sewage disposal plants, septic tanks or by other approved methods, conventionally, cattle waste is not so treated.

The United States has a population of approximately 275 million people and raises approximately 100 million cattle, of which over 32 million are brought together in CAFOs. If each adult animal produces 12 times as much waste as an adult human being, the United States is producing the animal waste-equivalent of a nation of 385 million people, just in feedyards. The U.S. has approximately 10 million head of dairy cows on feed annually, which produce the waste equivalent of 14 million beef cattle.

Consequently, ruminant animals, primarily beef cattle and dairy cows, are posing a substantial threat to the environment, despite their importance as human food sources. Cattle on farms and ranches average approximately one animal for each 12 acres or about one animal per 500,000 square feet, whereas, in a confined feedyard operation, one animal has an average of 250 square feet. This animal density concentrates the manure into very small areas and local ecosystems are thereby jeopardized.

CAFOs larger than 1,000 beef animal units (equivalent to 700 dairy cows) are the point source for numerous real and perceived environmental problems: water contamination, airborne particulates, objectionable odors, fly and insect infestations, nitrogen and phosphorus buildup in the soil and major fish kills in rivers and streams. In its Dec. 15, 2002 final rule (40 CFR Parts 9, 122 and 412), the U.S. Environmental Protection Agency (EPA) stated that its new regulations would ensure "that an estimated 15,500 CAFOs effectively manage the 300 million tons of manure that they produce annually." The troublesome greenhouse gas (GHG) emissions of methane is another major environmental problem. Worldwide, cattle are the single largest animal source of methane release into the environment (methane is 22 times more potent than $CO_2$ as a greenhouse gas).

Most states require freshly applied raw animal manure to be incorporated into the soil at prescribed depths and within 12 hours of manure application. This is the most "economic" use of feedyard manure today. Feedyards that recover manure but do not keep it separated and free from dirt contamination, will normally sell the pen scrapings in a dry form. However, this method is more labor intensive and requires additional equipment and real estate for wind row drying. At this point, the waste byproduct can pollute the surrounding environment if washed away during wet periods and the opportunity for odor and insect problems increases.

Another major environmental concern caused by CAFOs is the build-up of nitrogen and phosphorus in the soil where manure is applied or disposed of. This build-up comes from the long-term consumption, and then concentration, of feed grain in the relatively small area encompassed by a CAFO. For example, a typical feedyard will consume approximately 20 pounds of corn per animal per day. In a 25,000 head feedyard that is full with year-round operation, this amounts to approximately 3,250,000 bushels of corn per year.

In the corn belt of the upper Midwest each acre of corn receives approximately 135 pounds of nitrogen per acre and will yield approximately 130 bushels of corn per acre. When the mature corn is harvested only the seed is saved and the plant is reincorporated into the soil for nutritional enrichment. The 130 bushels of seed corn taken from the acre contain most of the nitrogen and phosphorus which is then transported to the cattle feedyard for feed rations. If a typical 25,000 head location utilizes 3.25 million bushels per year and the average production is 130 bushels per acre, the feedyard will require all of the output from 25,000 acres of corn.

If a conventional 25,000 head feedyard is built on approximately 250 acres of land, this means the nitrogen and phosphorus is taken from 25,000 acres of corn and ends up on 250 acres of feedlot—a concentration of 100-fold. During the feeding cycle, cattle use approximately one-half of the nitrogen in the corn for body growth by converting it to protein. Thus, this portion of the nitrogen leaves the feedyard as meat. Taking into account conversion factors, on balance, 66% of the nitrogen and 100% of the phosphorus is left behind. The manure management of the feedyard must then move these compounds back to local farm fields as replacement fertilizer needed for next year's crop, under EPA's new rules, with upper limits at the crop's "agronomic uptake levels."

If the feedyard does not collect and apply these compounds properly to the land, it will end up in the environment. Large portions of the nitrogen and phosphorus are typically transported off site via water runoff, airborne particulates, manure removal or disposal, etc. The principal environmental threat is that large volumes of nitrogen and phosphorus enter the water system, as in the widely reported instances of runoff from Midwestern states like Iowa and Illinois into the Mississippi River, and ultimate deposit in heavy concentrations in the Gulf of Mexico and elsewhere, causing immense "dead zones" which cause the death of shrimp and other fish due to oxygen depletion.

While anaerobic digestion of manure has been known for centuries, it has never been practiced on a large scale basis in cattle feedlots due to poor economics, inability to prevent manure contamination by soil and water and limited outlets for the bio-methane. It's practice by dairies has been limited due to marginal economics, largely driven by parasitic heat loss, and low revenue from biogas-generated electricity sales, as dairies have no economically useful demand for low pressure steam.

It is clear that a new approach to CAFOs is needed in order to address the concerns of environmental regulators, consumers, and the economic pressures facing the industry itself.

Recent outbreaks of *E. Coli*-contaminated meat, and growing consumer demand for "clean" beef have combined to put significant pressure on livestock producers, feedlot operators, and meat packers. In the U.S. conventional feeding methods rely upon heavy use of anabolic steroids, antibiotics, and other artificial practices to promote animal weight gain. However, the U.S. Food and Drug Administration (FDA) has expressed growing concern over the threat posed by excessive antibiotics use in animal feeding, which experts now link to the proliferation of drug-resistant bacteria, and increasing humans' vulnerability to untreatable infections.

Moreover, food safety officials have expressed growing concern about the long-term health effects of eating beef which contains high levels of antibiotics and growth hormones, and many nations prohibit the importation of U.S. beef that contains growth-enhancing steroids, hormones, and other "artificial" additives. Consequently, consumer export for U.S. beef has declined in recent years.

A recent Presidential Executive Order set a national goal of tripling the production and use of bio-fuels by the year 2010, in large part due to the need to achieve substantial reductions in emissions of greenhouse gases such as carbon dioxide ($CO_2$) and methane. Primary sources of $CO_2$ are fossil fuel combustion, and a primary source of methane emissions is cattle flatulence and manure. Renewable bio-fuels such as ethanol and bio-gas using conventional methods are not cost competitive with fossil fuels, and new approaches are needed if the production goals are to be met. One of the most capital- and energy-intensive sections of modern-day ethanol plants is the spent mash (protein co-product) drying and handling section. The protein co-product is valued as an effective feed ingredient for ruminant animals (cattle and dairy cows), but in traditional practice must be dried before it can be transported and stored. Eliminating this requirement would result in substantial capital, energy and operating cost savings in ethanol production. In addition, since Sep. 11, 2001, homeland security objectives dictate the need for dispersed and decentralized forms of energy production that can operate independently of conventional refineries, pipelines and even the electricity grid.

The invention as described and claimed in U.S. Pat. No. 6,355,456 addressed many of the foregoing problems by integrating an ethanol production unit with a cattle feedlot (or dairies) and thereby rationalized both the disposal of residue from the ethanol units and anaerobic digestion of ruminant animal waste. However, that prior invention still required some purchase of natural gas from an external source to supply the energy necessary for production of process steam, heat for operation of the ethanol units and, accordingly, the integrated bio-refinery (IBR) of the prior invention was not a wholly self-contained operation. Ammonia tended to build-up in the digester system, and the production of bio-gas from the digesters is significantly reduced by the ammonia build-up. The design of the previous invention was also limited in that it required a minimum number of cattle in the feed lot in order to justify digester operation. Another limitation of the prior invention as the high phosphorus and nitrogen content of the filtrate from the digester or the so-called "liquid fertilizer."

SUMMARY OF THE INVENTION

Accordingly, the present invention utilizes many features of the design of the invention described in U.S. Pat. No. 6,355,456 and further utilizes thin stillage from the ethanol unit to reduce ammonia build-up in the digesters and thereby increase bio-gas output. It has also been found that the addition of thin stillage from the ethanol unit bottoms to the manure digesters substantially increases bio-gas output beyond that which can be attributed to reduction in ammonia build-up.

Accordingly, the present invention represents a further integration of ethanol production and a cattle feedlot or dairy to further improve the economics of anaerobic digestion of livestock manure and of the ethanol production. Like the invention of U.S. Pat. No. 6,355,456, the present invention provides for continuous integration of the following three subsystems:

1. A CAFO which encloses livestock and provides for sanitary manure disposal, prevention of contamination of the manure, control of disease and climate protection for the cattle or dairy cows;

2. An anaerobic digestion/bio-fertilizer recovery system which collects manure from the CAFO, admixes it with thin stillage from the ethanol production unit and converts it into bio-methane and bio-fertilizer; and 3. An ethanol plant, without traditional spent grain mash drying equipment, and the process steam for which is provided by the bio-gas recovery energy system.

Integration of the above three "subsystems" in the present invention creates conditions suitable for cost-effective production of "clean beef" or milk, ethanol and bio-gas, and simultaneous reductions in environmental pollution linked to livestock feeding operations. Each of the three "subsystems" is dependent on the other, from the perspective of both operational and economic efficiencies. For example, the ethanol plant would require expensive mash drying equipment if there were no feedlot; the anaerobic digestion system could not be economically viable if the ethanol plant could not utilize its bio-methane, etc.

Accordingly, the present invention provides an integrated continuous process for the production of ethanol and methane, which process includes fermenting grain in an aqueous medium to produce ethanol, a bottoms residue and carbon dioxide; separating the ethanol from the residue; separating the residue into wet cake and thin stillage; feeding the wet cake to livestock; collecting manure produced from the livestock; admixing at least a portion of the collected manure and at least a portion of the thin stillage to produce an admixture which is digested to produce bio-gas, a liquid effluent, and a bio-fertilizer compost.

Preferably, the liquid effluent is treated for phosphorus removal by addition of a calcium compound and at least a portion of the carbon dioxide from the ethanol production to precipitate at least a portion of the phosphorus as calcium phosphate and to obtain a phosphorus depleted liquid. The calcium phosphate is then separated from the phosphorus depleted liquid. The former can be used as a fertilizer and the latter can be used for crop irrigation.

Preferably, the amount of stillage admixed with the collected manure is regulated to prevent build-up of ammonia and/or to maintain digestion of the manure at a temperature of at least 99° F.

The present invention provides the following advantages over the invention described and claimed in U.S. Pat. No. 6,355,456:

1) Eliminates need for a natural gas line, and for purchase of external natural gas, and replaces same entirely with internally-generated bio-gas to power boilers to generate process steam and heat for the ethanol unit and Integrated Bio-refinery (IBR) complex self-contained operations. In contradistinction to conventional practice, no coal or natural gas (fossil fuels) is required for renewable ethanol production. By eliminating the need for natural gas, ethanol production costs are reduced by $ 0.25-$0.35/gallon of the ethanol produced (based upon current natural gas costs). Thus, widespread commercialization of IBR's could open up rural locations across the country which do not have access to natural gas or rail lines.

2) Utilizes thin stillage from the ethanol unit in admixture with beef or dairy manure in the anaerobic digestion (AD) system to increase volatile solids content, and thus significantly increases bio-gas output, and simplifies the use of WDB in the total mixed ration.

3) Reduces ammonia buildup in the AD system (which can reduce bio-gas output) by adding thin stillage to manure (dilution) for conversion to bio-gas and bio-fertilizers.

4) Eliminates need for ethanol unit evaporators, dryers, and thermal oxidizers, further reducing energy requirements and capital costs, as well as costs of operation and maintenance.

5) Maximizes operational flexibility in IBR complexes, by permitting a wide range of variability in beef and/or dairy animal numbers (even compensating for an extreme event of "zero occupancy"), yet still allowing continuation of ethanol plant operations. This is achieved by designing the AD system to process both thin stillage and "wet cake" from the ethanol unit, such that it can partially, or completely, substitute for manure feedstock, and continue to generate bio-gas and bio-fertilizers.

6) Better enables beef and dairy operations compliance with Dec. 16, 2002 CAFO rules by facilitating phosphorus (P) and nitrogen (N) nutrient removal from AD system filtrate. Admixture of thin stillage from ethanol unit and manure from beef and/or dairy animals fed "wet cake"-rich rations concentrates P and N in AD system digestate. Separation of the digested product into liquid fraction (filtrate) and bio-solids is done via physical methods. The filtrate fraction can then be treated physically, and chemically (e.g., precipitation) to remove N and P. Pre-treatment of manure and thin stillage in an AD system makes them both more susceptible to efficient removal techniques. In a preferred embodiment, IBR complex carbon dioxide ($CO_2$) by-product from the ethanol unit can be used in nutrient removal unit to reduce pH after lime or other precipitating agents are added, further promoting phosphorus removal.

7) Achieves maximum conservation and recycle of water from complex operations (including beef and dairy urine in the AD system) by sending treated "clear filtrate" back to adjacent fields as irrigation water, and utilizing recovered P and N nutrients, along with AD system bio-solids, as soil amendment materials for farmland, golf courses, sod farms, etc. In a preferred embodiment, the "clear filtrate" water is fully treated by reverse osmosis or other methods to enable its use in the ethanol plant as process water.

8) "Post-9/11", community-sized, dispersed, decentralized, "off-the grid" renewable liquid and gaseous fuels production is made commercially possible. IBR's employing the present invention will require no rail, and no natural gas, lines. In addition, such complexes provide defense against food security threats, including Bovine Spongiform Encephalopathy (BSE), and terrorist threats to the meat and milk system, by enabling a verifiable feed ration compliance system that can be internally enforced.

9) The present invention, due to its closed-loop, insulated, synergistic process that virtually eliminates the use of fossil fuels, provides maximum environmental benefits, including conformance with recent CAFO regulations; greenhouse gas emission reductions; and greatly reduced air and water pollution, including odors. AD-derived soil amendment materials can be used profitably to not only reduce hydrocarbon-derived fertilizer usage, but also improve soil quality and sustainability for the future.

10) The livestock enclosures, which are deliberately positioned to face south, can be equipped with photovoltaic arrays to generate electricity from the sun, thereby making the complex independent of the electricity grid, as well.

The present invention also provides the following additional advantages:

1. It integrates a CAFO with ethanol production in such a manner that the economics of both the ethanol production and the feedlot or dairy operation are enhanced.

2. It integrates anaerobic digestion of livestock waste with ethanol production in such a manner that the economics of both the ethanol production and the anaerobic digestion are enhanced.

3. It provides a ruminant CAFO with a "natural" feed that is efficient in terms of weight gain, that can justify the reduction in use of anabolic steroids and antibiotics, and that reduces livestock flatulence (a source of methane emissions linked to global warming).

4. It provides a wet cake as a feed ration component for beef and/or dairy cattle such that conversion efficiencies and the animals' health are significantly improved.

5. It reduces the incidence of *E. coli* in beef cattle by utilizing a "high saturation" feed ration (ethanol unit wet cake) to reduce acidosis, typically caused by excessive starch in the feeding ration.

6. It provides a high protein feed, in required quality and quantities, for ruminant animals by locating the ethanol unit adjacent to their confinement location, thus eliminating long distance transport and the need for expensive drying.

7. It utilizes the "natural" concentrated protein in the separated ethanol unit wet cake to improve the starch:protein balance of the traditional cattle ration, and enables the replacement of external protein sources such as urea and alfalfa hay, thus reducing feeding costs and simplifying a cattle operation's sourcing and inventory requirements.

8. It reduces/eliminates cattle feedlot odor and water contamination by rapid transfer of the cattle waste into the anaerobic digestion system, and destruction of the pathogens by the conversion of the cattle waste into bio-gas, bio-fertilizer, and bio-sludge.

9. It makes the production of the ethanol and bio-gas bio-fuels more cost competitive with fossil fuels, by exploiting synergies to reduce capital and operating costs, and maximizing returns on all of the co-products.

10. It eliminates the need for the capital intensive, and costly to operate and maintain, spent grain mash drying equipment in the ethanol plant, including thermal oxidizers now required by environmental authorities to reduce harmful emissions caused by the driers.

11. It substantially reduces the emissions of greenhouse gases such as $CO_2$, methane, and nitrogen oxides to the atmosphere, thus reducing the threat of global warming.

12. It reduces the use of fossil fuel fertilizers, and breaks the nitrogen/phosphate build-up cycle that is causing massive "dead zones" in the Gulf of Mexico and other waterways due to field runoff.

13. It balances the sizes of the ethanol unit and the feedlot so that all of the high protein WDGS can be fed "wet" directly to the cattle, without capital- and energy-intensive drying, and freight. Compared to a conventional ethanol plant of the same capacity, the present invention's simplified ethanol plant's capital costs will be reduced by up to 30%. In effect, the present invention's ethanol unit serves dual purposes as the feed pretreatment center for "clean beef" or milk, and as a plant for producing ethanol as a "co-product".

14. It reduces operation and maintenance requirements and overall labor costs. The most important simplifying factor is the elimination of equipment and process duplication in grain handling, energy systems, infrastructure, transportation, etc. However, other operating benefits come from the enclosure of the cattle, the easy proximity of the ethanol wet cake (WDGS) for ration formulation, and the improved management of the manure.

The teachings of U.S. Pat. No. 6,355,456, inclusive of the specification, claims and drawings, are hereby incorporated herein by reference.

BRIEF DESCRIPTION OF THE DRAWINGS

FIGS. 2A and 2B are, respectively, plan and side views of a preferred cattle feeding pen.

DESCRIPTION OF THE PREFERRED EMBODIMENTS

Figure 1:
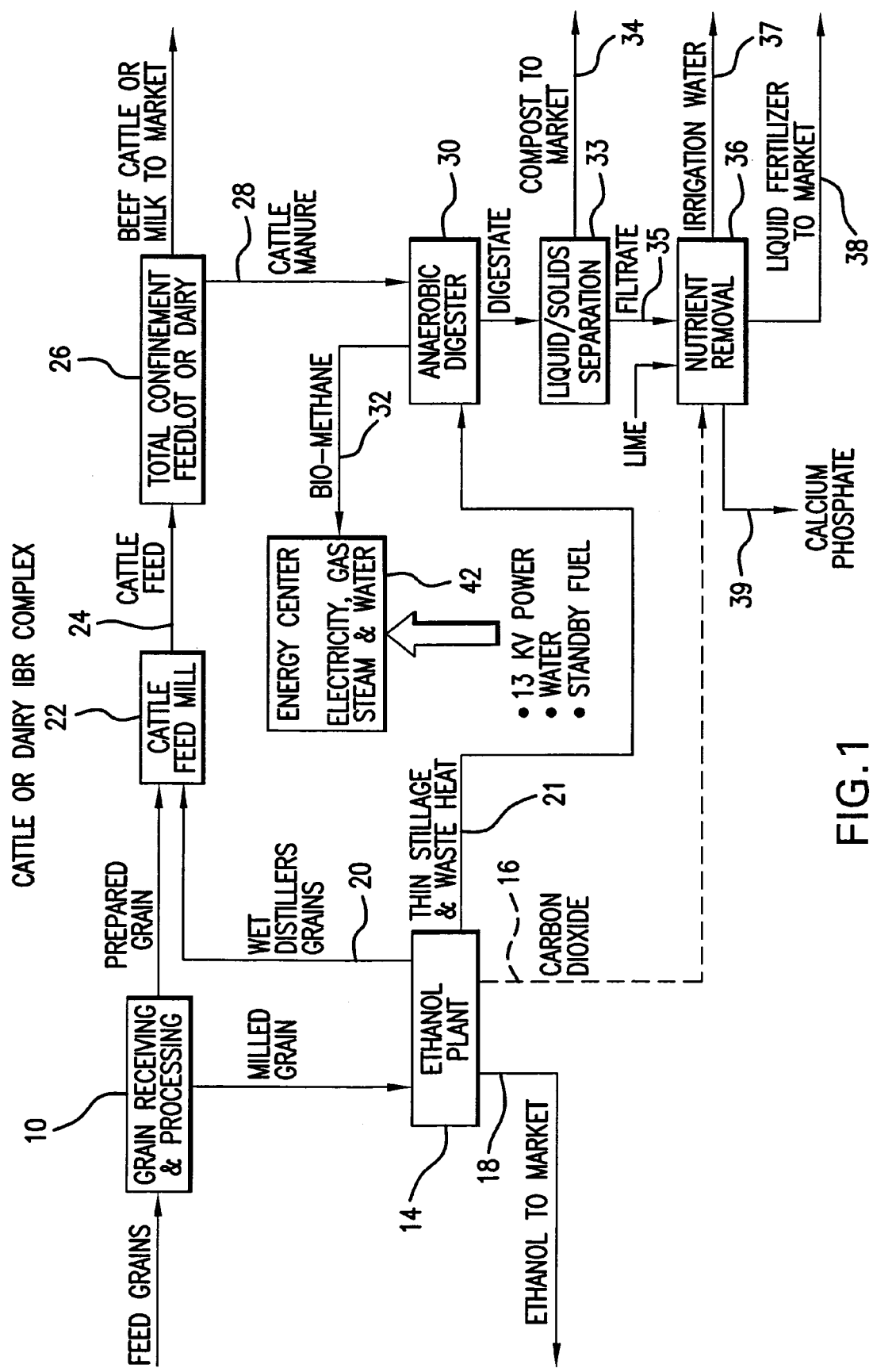
FIG. 1 is a block diagram of a preferred embodiment of the present invention in which the three primary subsystems, along with the common energy complex, are integrated in a continuous operation for the production of "clean beef" or milk, ethanol, wet cake—distillers' grains with solubles (WDGS), and bio-gas/bio-fertilizer/bio-solids.

FIG. 1 depicts the process with illustration of the major apparatus components utilized therein. Corn from a grain receiving unit 10 is fed to a conventional milling device, preferably like those used in "dry mill" ethanol plants, for preparing the feed to the ethanol plant (fermenters) 14. The major products of the fermentation are carbon dioxide 16, ethanol 18, and "wet cake" (WDG) 20, waste heat, and thin stillage 21. The wet cake 20 is fed to a feed mixer 22 wherein it is blended with a ratio of wet cake:grain of 25:75 to 80:20. The mixed feed 24 is then passed to an enclosed cattle feedlot or dairy 26 where cattle or other livestock are fattened prior to processing, or milk is produced. The animals can be slaughtered and routed to an on-site meat packing plant to produce a high quality product. Manure 28 is collected from the enclosed CAFO and fed to digesters 30 to produce a bio-gas (principally methane) 32 and the residue is introduced into a solids/liquid separator and solids drying system (typically wind-rowed by solar) 33 to produce a clean fertilizer compost 34. The liquid filtrate 35 goes to nutrient removal 36 to produce irrigation water 37 and liquid fertilizers 38. The bio-gas is routed to an energy conversion unit 42 which utilizes non-fossil energy to run the integrated complex. The liquid effluent from separator/dryer 33 is treated at 38 (e.g., a tank) by addition of lime (CaO) and $CO_2$ from the ethanol unit 14. The energy conversion device may use steam boilers to generate steam for the ethanol unit, with excess gas then used to generate electricity, or other combinations. The manure digester 30 is either a mechanically mixed, or a plug-flow, or a fixed-bed reactor type.

Ethanol Synthesis

The ethanol synthesis unit 14 may employ a variety of fermentation organisms, ranging from conventional yeast strains used in most modern ethanol plants, to advanced fermentation organisms such as *Zymomonas mobilis,* the benefits of which are described in U.S. Pat. No. 4,731,329 issued to Lawford, and U.S. Pat. No. 5,070,016 issued to Hallberg. In a preferred embodiment, where the ethanol unit is capable of processing not only the seed portion of the corn, but also cellulosic feedstocks such as the cornstalks thereby lowering raw,material costs, the use of *Zymomonas mobilis*-type organisms would be practiced.

As taught in U.S. Pat. No. 6,355,456, the teachings of which are incorporated herein by reference, conventional ethanol plants ferment starch in grain materials to ethanol and carbon dioxide, and centrifuge, evaporate, and dry protein co-products to allow for shipment (truck and rail) to off-site beef and dairy feeding operations. Protein drying operations are highly energy intensive, and require heavy capital investment, including, in addition to the dryers, evaporators and thermal oxidizers now required by the EPA to capture harmful emissions.

IBR ethanol units do not dry the protein co-product, and thus can eliminate most of the "back end" units, including the evaporators and thermal oxidizer. The centrifugation system in 14 is used to separate the "still bottoms" into both "wet cake" and "thin stillage". In a departure from the teachings of U.S. Pat. No. 6,355,456, the preferred embodiment of an IBR will send the wet cake (approximately 35% solids, with a protein content of approximately 30%) to the on-site feed mill, where it will be added, in mill 22, to a balanced total mixed ration specifically contoured to the nutritional requirements of either the beef or dairy animals on-site. The thin stillage 21, at a temperature of approximately 165° F., is pumped to the AD system holding tanks 30, where it will be used in an admixture with the "clean manure" feedstock captured from the beef feedlot or dairy feeding parlors.

Because the ethanol unit 14 will not dry the protein co-product, conventional ethanol plant energy requirements will be reduced by as much as 40% or more. The boilers (unit 42) required for steam generation can be reduced commensurately. In addition, these boilers will be modified so that they can efficiently utilize higher sulfur bio-gas, which will be used to supply 100% of the IBR complex steam requirements.

To provide backup and redundancy in the event of temporary upsets, a supplementary fuel source is provided, and the boilers (unit 42) are preferably equipped for use of both bio-gas and the stand-by fuel (propane, fuel oil, diesel, etc.).

The ethanol unit feedmill 12 will be capable of handling wide swings in "wet cake" addition to the beef or dairy TMR, ranging from 25-80%, as taught in U.S. Pat. No. 6,355,456. The complex will be specifically designed to enable full operation of the ethanol unit, even in the unexpected event of a large reduction in, or even total loss of, beef or dairy animal numbers. In such an event, ethanol operations can be maintained by routing all of the "wet cake", and thin stillage, to the AD unit, where it will be converted to both bio-gas and bio-fertilizers.

In the case of both beef and dairy operations, whether new complexes are built ("greenfield" operations) or "insertions" are made into existing operations, the key for efficient IBR operation is to ensure the earliest possible retrieval and transport of "clean manure" to the AD system's vessels. The earlier the manure is sent to the AD system's "bugs", the better: higher bio-gas output; greater reductions in odor; and maximum reductions in emissions of GHG's, especially methane release to the atmosphere.

U.S. Pat. No. 6,355,456 placed heavy emphasis on the use of slatted floors for beef feedlots, to teach the importance of recovering "clean manure" that is free of dirt, sand, and excess water. However, any technique may be used: scrapers; vacuum pumps; or combination of processes, so long as the manure quality is controlled for the purpose of enabling its optimal conversion to bio-gas for use in a modified on-site ethanol unit, and bio-fertilizers.

The operation of the ethanol synthesis unit 14 employed in the present invention is otherwise identical to those in operation today, with the important exception of the spent grain (protein byproduct) drying equipment and evaporator. The present invention makes possible the elimination of this equipment, resulting in approximately 30% less capital cost, and substantial reductions in plant energy, labor and operations and maintenance costs.

The Feedlot

Figure 2B:
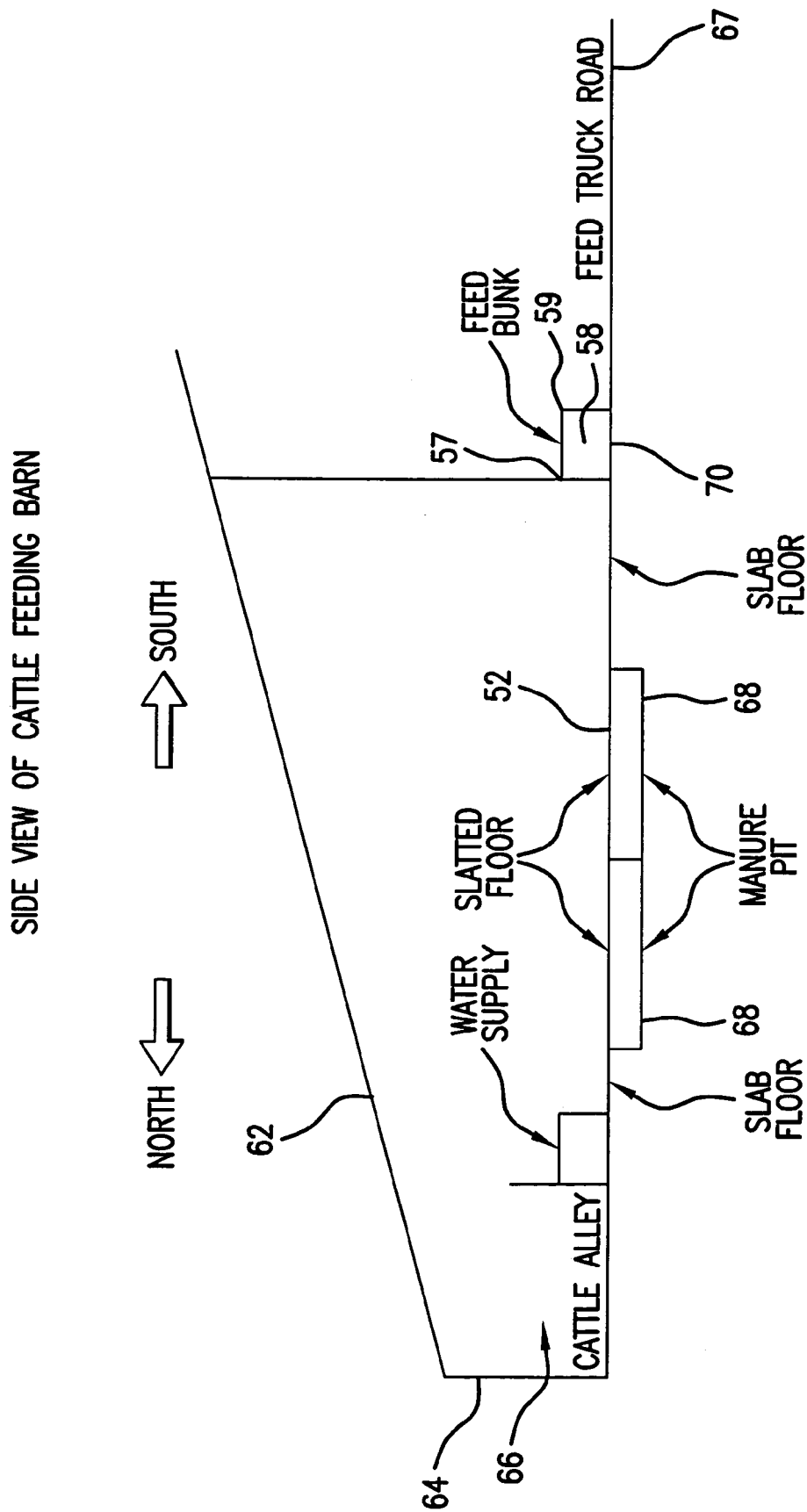

FIGS. 2A and 2B illustrate the preferred embodiment of the manure collection, cattle feeding confinement facility, or feedyard. In its preferred embodiment, a shed 66 encloses pens 50 which are constructed so that each animal has approximately 25-30 square feet of floor space. For descriptive purposes, a feedyard with 28,800 head enclosed capacity would have some of the following characteristics: Each pen 50 would measure 40 feet deep by 60 feet long, 100 head each. The floor is constructed of slatted concrete panels that are 4 feet wide and 12 feet long. There are two panels 52 laid end to end for a 24×4 foot floor 54. The floor panels are formed of reinforced concrete slats. Each concrete slat is 4" wide and the spacing between adjacent slots is 1.5".

The pens 50 are covered by a roof 62 that is much higher at the front than the rear. This allows for rain and snow coverage and runoff. The front of the shed 48 is facing south. This allows for maximum light, all day. The design takes advantage of the summer and the winter solstice. In a preferred embodiment, photovoltaic arrays may be installed along part of the roof to convert sunlight into electricity. During the winter, the sun shines all the way to the back of the pens 50. During the summer, the pens are shaded. Each shed 66 is enclosed on the east and west sides. The back or north side has ventilation slats 64 that can be manually adjusted. In addition, two back panels may be added for weather and temperature control in late fall and early winter. During the winter, the pen is protected from the north wind and snow, and provides the animals with a dry, warm environment compared to conventional, open dirt floor confinement facilities.

Beneath the slatted floor 52 is a shallow trough 68, which directs the manure into the initial preparation tanks of the anaerobic digester. Depending upon circumstances, the floor can be scraped, gravity-flowed, or pumped to move the manure to the AD vessels.

The pens 50 are gated at the back into a paved feed truck road 67, which allows the entry and exit of the cattle. The paving is important, as it prevents dirt and foreign materials from getting into the manure, and contaminating the anaerobic digestion system.

Concrete-constructed feed bunks 58 are located on a paved alleyway at the front of the pens and run the entire length of the pen row. The feed bunk 58 has a front panel 59 higher than rear panel 51 to prevent spillage. Feeding occurs twice daily, or more if needed. Each animal is provided 6 to 8 inches of bunk space on average and eats off and on all day. When the cattle are not eating, they lay in the back of the pen while others are feeding. A feed delivery truck brings the special "high saturation" WDGS ration that is prepared fresh daily for each pen. Access for the feed delivery truck is provided by an easily accessible feed alley 67. A concrete mat 70 is provided under the feed bank 58. The concrete mat 70 helps with clean-up and is sloped to prevent surface water from entering subfloor sites.

The Dairy

Figure 3:
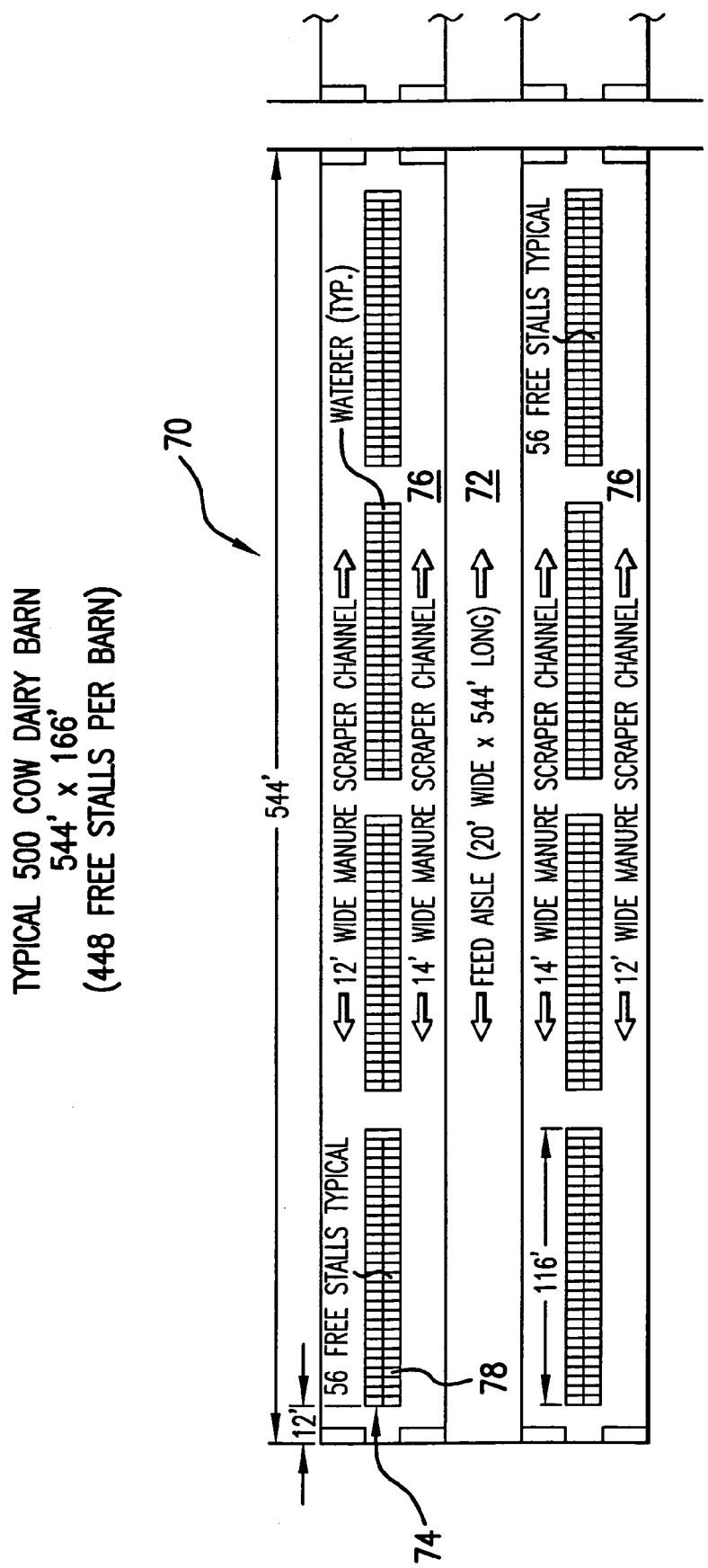
FIG. 3 is a plan view of a preferred diary parlor used in the present invention.

Each dairy site ideally consists of six main free stall barns 70 which are typically 544×100', each housing 500 cows using a 4 row barn design, assuming a stocking rate of 110 percent of total freestalls. See FIG. 3 for layout of a typical dairy barn.

Within each free stall barn 70, feed alleys 72 are provided that are wide enough to allow the feed trucks to deliver the total mixed ration to the feedlines. The feedlines provide for 24 inches per cow at the feedline. Each barn 70 also contains four rows 74 of freestalls 78 consisting of approximately 450 freestalls and two cow alleys 76 on each side of the center feed alley 72.

The milking parlors may utilize a rotating parlor system, a parallel milking parlor or other milking parlor system that will allow the operator to handle the milking cows in 6 to 7 hours, allowing for time to clean the system between milkings to maintain sanitation in the parlor system.

For climate control, the barns 70 have insulated roofs to maintain heat in winter and to limit solar heating during the summer. The barns 70 will also be equipped with a curtain system that will allow the curtains to be controlled manually or by temperature and humidity sensors. The purpose of the curtain system is to maintain the heat generated by the animals within the barn 70 during the cold weather months, while at the same time allowing for the cows to have an outdoor atmosphere when the curtains can be opened during the warmer seasons.

To maintain climate control during hot weather, the barns 70 are preferably equipped with high volume fans to cool the cows during hot weather. Preferably, water misters are installed over the feeding area as well as in the cow holding area, to cool the cows in very hot weather. Automatic cattle water tanks are located throughout the freestall barns 70.

The freestalls 78 are located on an elevated area to keep the cows dry. Each freestall 78 is 4' wide, with each being divided by a stainless steel freestall divider pipe. They may be equipped with rubber mats, water beds or other bedding to provide a comfortable place for the cows to rest between feeding and milking. The preferred freestall bedding is compost from the anaerobic digester 30, which is available on site.

The cow alleys 76 are normally made of concrete that have grooves cut into them for firmer footing for the cows to walk on. Some alleys 76 may also be equipped with a rubber mat down one side to allow the cows to walk on rubber rather than concrete. These are especially useful in high traffic areas such as the main alley 72 leading to the dairy parlor.

Anaerobic Digestion

Anaerobic digesters 30 ("AD system" or "AD units") are mechanical devices that utilize biological organisms in the absence of oxygen to convert cattle manure and other residual streams into marketable by-products. A properly operated digester will eliminate manure odors, destroy the pathogens and convert the manure to bio-gas, liquid fertilizer and compost which can be sources of income for the feedyard. In addition, the environment and neighboring areas are vastly improved.

To obtain maximum use of waste heat from the ethanol unit 14, thin stillage is added to manure admixture to maintain the AD unit 30 temperatures at 99° F. or more (depending upon whether it is a mesophilic or thermophilic operation), either of which can be used in an IBR complex. "Parisitic heat loss" from conventional AD systems can require the use of 50% or more of the bio-gas produced to maintain the AD unit's temperature levels. As maximum bio-gas output for use in the ethanol unit boilers is a primary objective, maximum heat efficiency is achieved from the combination of transfer of ethanol unit waste heat from the cooling towers, and the 165° F. thin stillage.

The AD unit 30 will be continuously supplied with an admixture of beef and/or dairy cattle manure 28, and thin stillage 21 and waste heat from the ethanol unit 14. The thin stillage will be metered in with the manure so as to provide maximum dilution effect in order to control, even prevent, ammonia build-up in the reactor of the AD unit 30. Ammonia buildup in AD systems has been proven to significantly interfere with the anaerobic digestion of the volatile solids in the vessel and, unless controlled, can significantly reduce bio-gas output. Serendipitously, thin stillage also is rich in digestible materials, further increasing biogas output.

Depending upon the exact techniques employed in an AD system, bio-gas output is measured by the methane equivalent ($CH_4$-equivalent) of bio-gas generated, as measured on the amount of bio-gas produced from volatile solids (VS) "as destructed". Thin-stillage yields 90% of volatile solids destructed, compared to dairy manure's 45%. Thus, thin stillage produces twice as much bio-gas per pound of VS added as does ruminant animal manure.

Consequently, a standard-sized IBR complex (20 million GPY ethanol unit, 28,800 head feedlot) could expect approximately 50% displacement of natural gas by bio-gas from manure digestion only, but more than 100% natural gas displacement when the thin stillage is added to the manure. As natural gas costs continue to climb, this capability of integrated complexes using the present invention to entirely eliminate purchased natural gas reduces the cost of producing ethanol by $0.25-$0.35/gallon of ethanol.

The AD unit 30 is also designed so that, in the event of unexpected reductions—even to the point of "zero vacancy"—in the beef and/or dairy animal numbers, the ethanol unit can continue operations by diverting both the thin stillage and wet cake streams to the AD system. This provides critically important flexibility, and is a major selling point to lenders, in particular, to insulate against worst-case scenarios.

Treatment of Liquid Effluent from A/D Units

As foreseen in U.S. Pat. No. 6,355,456, the U.S. Environmental Protection Agency (EPA) did release final regulations governing CAFO's in excess of 1,000 animal units (with one animal unit equal to a 1,000 lb. beef steer, thus 700 1,400 lb. dairy cows). These strict new regulations, which come into force for existing operations on Jan. 1, 2007, pose particular challenges in the case of land application of both nitrogen (N), and phosphorus (P) found in animal manure.

As explained above, the combination of manure from animals fed wet cake-rich rations, and thin stillage from a co-located ethanol unit, offers substantial benefits in terms of capital, operating, and energy cost reductions compared to conventional practice. However, this approach also concentrates the amounts of N and P found in the AD system digestate, which is separated in unit 33 into its bio-solids and liquid fractions (filtrate). For a standard-sized IBR complex, tens of thousands of acres of adjacent irrigated farmland will be required to comply with the P soil loading limits imposed by the new CAFO rules.

In order to provide greater siting flexibility, and to generate valuable new revenue streams for IBR complexes and their owners, nutrient removal and recovery techniques are now in the process of being adapted from municipal applications, and applied to CAFO operations. A significant advantage of the IBR method proposed in the present invention is that it makes investments in AD systems economically attractive, and the treatment of raw manure in AD systems is a critically important first step for most nutrient removal processes.

For both N and P removal, a myriad of physical and chemical techniques are being evaluated. In the case of P removal, which promises to be the most challenging, removal of P from the AD system filtrate will in many cases utilize chemical precipitation methods. For example, one such method employs a calcium compound, preferably lime, to precipitate soluble phosphorus out as basic calcium phosphate 39. The lime addition raises the solution pH to 11 or more, slowing or stopping the reaction. To further the reaction, and thus more completely remove the phosphorus from the solution, it is necessary to reduce the pH to about 10 or less to restart the reaction. Typically, in municipal settings, this is best done using carbon dioxide.

Thus, in the preferred embodiment of the present invention, the carbon dioxide 16 from the on-site ethanol unit 14 is utilized for pH adjustment in the nutrient removal section 36, thus producing a phosphorus depleted liquid 37 (essentially water) suitable for field irrigation and a calcium phosphate solid 39 suitable for use as a fertilizer. This represents significant savings compared to current practice in terms of elimination of costly carbon dioxide compression and transport requirements.

Methane Utilization

In addition to its ability to generate bio-gas, and to protect against water contamination and odor pollution, the most significant attribute of the anaerobic digester is its ability to greatly reduce, if not eliminate, the environmental release of methane gas from cattle feedlots. Animal manure rapidly degrades into methane gas. Worldwide, cattle are the largest non-industrial source of methane emissions into the atmosphere.

As the anaerobic digester converts digestible organics in the manure to biogas, the gas is extracted and, if necessary, "scrubbed" for use as a fuel in unit 42. With the present invention, the biogas recovered from the anaerobic digestion operation can be utilized in the complex to generate needed steam and to replace fossil fuel-generated electricity which would otherwise be purchased from local utilities. Any excess can be sold back to the electrical grid, and would be eligible for "green or renewable power tax credits" which makes this electricity more valuable than fossil fuel produced power. Under newly proposed federal legislation, in the near future, greenhouse gas credits (GHGC's) may have a monetary value which is currently estimated to be approximately $10 to $20 per ton of carbon equivalent (methane is 22 times as potent a GHG than carbon dioxide).

If the methane is first used to power electricity-producing devices, the exhaust heat can also be recovered and used to heat water for steam purposes. Steam too, can be successfully utilized by the feedyard for its source of flaking corn. In the preferred embodiment, by using a mechanically mixed anaerobic digester for manure management, relatively "clean" medium-BTU bio-gas (700-800 BTU's per cubic foot) is produced. It is optional to recover hydrogen sulfide and other harmful sulfur components prior to taking the biogas to the boiler or turbine. This bio-gas is then used in on-site for generation of electricity and "waste" steam. The low-pressure steam is perfect for use in the ethanol unit, and feedmill.

Greenhouse Gas (GHG) Reduction

Compared to conventional practice, the present invention will substantially reduce GHG emissions of $CO_2$, methane and nitrogen oxides.

Carbon Dioxide

Carbon dioxide emissions are reduced through the following:

1) The primary raw material of the present invention is corn or other feed grain. During photosynthesis, an acre of corn extracts more $CO_2$ than two acres of mature Amazon rain forest. Only the seed of the corn plant is used, with the rest returned to the earth where it acts as a "carbon sink". As noted below, surface application of the bio-fertilizer from the complex also allows the use of low input ridge till farming, as opposed to the more energy intensive "deep plowing" practices. This significantly reduces fossil fuel usage, and further augments the "carbon sink" effect, which helps to prevent soil erosion.

2) Due to the elimination of mash and protein byproduct drying, and the use of bio-methane instead of natural gas or other fossil fuels, ethanol is produced with a highly positive energy balance. Renewable ethanol, when substituted for petroleum-based fuels, reduces imported oil use on a 2:1 basis (two gallons of crude oil displaced for each gallon of ethanol used as an octane enhancer).

3) Utilizing the same bushel of corn to produce both meat and fuel results in extremely high conversion efficiencies, and substantially reduces petroleum consumption per bushel of corn produced (field preparation, cultivation, harvesting, fertilizers, chemicals, and transport).

4) Bio-fertilizer recapture and pathogen extermination (odor removal) allows energy efficient surface application back to the fields, and reduces petroleum and natural gas requirements for fertilizer manufacture, transport, and application.

5) Complexes utilizing the present invention are able to utilize high moisture (24% per bushel moisture content) corn picked directly from the field. This eliminates the energy normally consumed in corn drying (typically 14-15% moisture levels), and the petroleum consumed in transportation to and from the fields and the drying points.

6) Processing of both food and fuel at the same location will reduce overall transportation-related petroleum requirements, and costs, by 25% or more.

7) Feeding WDGS avoids not only the energy costs of drying, but also replaces petroleum-based urea in the feed ration.

8) In the preferred embodiment of the present invention, the capture and use of the $CO_2$ from the ethanol unit for phosphorous removal, meat processing and other purposes prevents its venting to the atmosphere, and saves fossil fuel-generated electricity used in both refrigeration and chemical processing for meat sterilization and transportation.

Methane (22 times more potent than $CO_2$ as a GHG)

Methane emissions are reduced through the following mechanisms:

1) By changing feed rations from predominantly dry corn to corn and WDGS, cattle flatulence is reduced by as much as 50%. By immediately. capturing the manure, most of the methane emissions to the atmosphere from the manure are also eliminated. Livestock-related methane releases account for a substantial portion of U.S. methane emissions.

2) The bio-gas recovered from the manure will be used to replace natural gas and other fossil fuels used for both electrical and steam generation (bio-fuels displace essentially 100% of the fossil fuel requirements of the entire complex). In large operations, excess energy can be sold to the grid.

3) The bio-fertilizer is pathogen-free, which allows surface application back to the fields (even while crop growth is occurring), and the use of low input ridge till farming instead of deep plowing. This further reduces petroleum requirements.

Nitrogen Oxides (210 Times More Potent than $CO_2$ as a GHG)

$N_2O$ emissions are reduced by the displacement of 50% or more of the fossil fuel-derived fertilizers by the IBR's bio-fertilizers. Conventional fertilizers are a major source of worldwide $N_2O$ emissions. In addition, bio-fertilizers are more readily available to the plant, further reducing $N_2O$ loss to the atmosphere.

In summary, the present invention substantially reduces fossil fuel use, livestock methane emissions and other pollution, and transform wastes into valuable products. As a result, substantial reductions in GHGs are achieved cost effectively, and efficiently. The net effect of these reductions should be of great benefit to the agricultural sector in the future as mechanisms are established for trading greenhouse gas emission reduction credits.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. An integrated continuous process for the production of ethanol and biogas comprising:
   fermenting grain in an aqueous medium to produce ethanol in said medium, a residue, and carbon dioxide;
   separating the ethanol and residue;
   separating the residue into wet cake and thin stillage;
   feeding the wet cake to livestock, said wet grain residue constituting 25-80% of a feed ration of said livestock on a dry weight basis;
   collecting manure produced by the livestock;
   admixing, at least a portion of the collected manure and at least a portion of the thin stillage to produce an admixture; and
   digesting the admixture to produce bio-gas, a liquid effluent and, as a residue, a bio-fertilizer.

2. A process according to claim 1 further comprising:
   dry milling the grain fed to said fermenting for producing ethanol utilizing the energy produced by combusting said biogas.

3. A process according to claim 1 further comprising milling the grain prior to fermenting.

4. A process according to claim 1, wherein said digesting is either plug flow or mechanical mixed digestion.

5. A process according to claim 1, wherein the wet cake from the ethanol production is fed to the livestock without drying.

6. A process according to claim 1, wherein said fermenting produces said wet cake in an amount substantially equal to 25-80% of a total feed requirement of said livestock.

7. A process according to claim 1, wherein:
   the amount of stillage in admixture with collected manure is regulated, along with the transfer of waste heat from the ethanol unit, to maintain said digesting at a temperature of at least 99° F.

8. A process according to claim 1, wherein:
   the amount of stillage in admixture with collected manure is regulated, to prevent build-up of ammonia in a digester in which said digesting is effected.

9. An integrated continuous process for the production of ethanol, a biofertilizer, calcium phosphate, and bio-gas comprising:
   fermenting grain in an aqueous medium to produce ethanol in said medium, a residue, and carbon dioxide;
   separating the ethanol and residue;
   separating the residue into wet cake and thin stillage;
   feeding the wet cake to livestock, said wet grain residue constituting 25-80% of a feed ration of said livestock on a dry weight basis;
   collecting manure produced by the livestock;
   admixing at least a portion of the collected manure and at least a portion of the thin stillage to produce an admixture;
   digesting the admixture to produce bio-gas, a liquid effluent containing phosphorus, and as a residue, biofertilizer;
   separating the liquid effluent from the residue;
   adding a calcium compound and at least a portion of the carbon dioxide to the liquid effluent to precipitate at least a portion of the phosphorous as calcium phosphate and obtain a phosphorous depleted liquid; and
   separating the calcium phosphate from the phosphorous depleted liquid.

10. A process according to claim 9, wherein said calcium compound is lime.

* * * * *